United States Patent [19]

Stenzel et al.

[11] Patent Number: 4,935,414
[45] Date of Patent: Jun. 19, 1990

[54] NEW INDOLYLPROPANOLS, PROCESSES FOR THEIR PREPARATION AND THEIR USE, AND PREPARATIONS CONTAINING THE COMPOUNDS

[75] Inventors: Wolfgang Stenzel, Reinbek; Ben Armah; Thomas Beuttler, both of Hamburg, all of Fed. Rep. of Germany

[73] Assignee: Beiersdorf AG, Hamburg, Fed. Rep. of Germany

[21] Appl. No.: 207,997

[22] Filed: Jun. 17, 1988

[30] Foreign Application Priority Data

Jun. 27, 1987 [DE] Fed. Rep. of Germany ....... 3721260

[51] Int. Cl.$^5$ ................. C07D 403/12; C07D 403/14; C07D 401/10; A61K 31/40
[52] U.S. Cl. ................... 514/210; 514/218; 514/253; 514/339; 540/575; 544/360; 544/373; 546/273; 548/467
[58] Field of Search ............... 546/273; 548/467, 468; 514/339, 414, 210

[56] References Cited

U.S. PATENT DOCUMENTS 4,137,331  1/1979  Berthold et al. .................... 548/467
4,304,915 12/1981  Berthold ............................. 548/467

FOREIGN PATENT DOCUMENTS 0025111  3/1981  European Pat. Off. .
2651574  5/1978  Fed. Rep. of Germany .
2737630  3/1979  Fed. Rep. of Germany .
2824677 12/1979  Fed. Rep. of Germany .
3200304  8/1982  Fed. Rep. of Germany .
3331612  8/1984  Fed. Rep. of Germany .
3524955  1/1986  Fed. Rep. of Germany .
3602304  8/1986  Fed. Rep. of Germany .

OTHER PUBLICATIONS

Scholtysik et al. Chemical Abstracts, vol. 103 (35401) 1986.
Berthold et al., Chemical Abstracts, vol. 106, No. 84635 (1987).
Takahashi et al., Chemical Abstracts vol. 107 (1987) (17504).
Romey et al., Chemical Abstracts, vol. 106, 1987 168709.
Scholtysik et al., Chemical Abstracts, vol. 106, 1987 12653.
Salzmann et al., Chemical Abstracts, vol. 105, 1986 202947.
Berthold et al., Chemical Abstracts, (Heterocycles) vol. 105, 1986 172505.
Scholtysik et al., Chemical Abstracts, (Pharmacology), vol. 105, 1986 54355.
Kohlardt et al., Chemical Abstracts, vol. 104, 1986 (199843).
Scholtysik et al., Chemical Abstracts, vol. 103, 1985 (81474).

Pharmazeutische Wirkstoffe, (Verlag) Stuttgart 1987, p. 391.

Primary Examiner—Mukund J. Shah
Assistant Examiner—E. Bernhardt
Attorney, Agent, or Firm—Sprung, Horn, Kramer & Woods

[57] ABSTRACT

Substituted indolylpropanols of the formula I

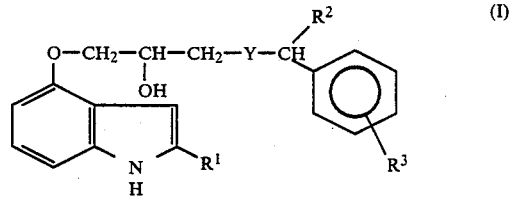

in which
$R^1$ denotes a cyano, carboxamido, alkoxycarbonyl, hydroxyl or acetyl group,
Y stands for the group A

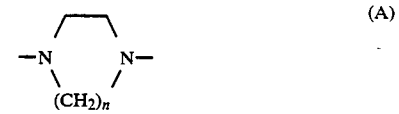

wherein n is the number 2 or 3, or the group B,

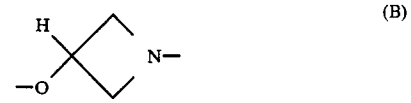

$R^2$ stands for $R^{2'}$ where Y denotes the group A and for $R^{2''}$ when Y denotes the group B, where
$R^{2'}$ denotes pyridinyl, thienyl or substituted phenyl which is monosubstituted or disubstituted by difluoromethoxy, difluoromethylthio, trifluoromethoxy, trifluoromethylthio, trifluoroethoxy, alkoxyalkoxy, cycloalkylalkoxy, alkoxyalkyl, alkylthioalkoxy, alkylsulphinylalkoxy, alkylsulphonylalkoxy, alkoxyalkylthio, alkoxyalkylsulphinyl, alkoxyalkylsulphonyl, alkylthioalkyl, alkylsulphinylalkyl, alkylsulphonylalkyl and dialkylaminoalkoxy, and
$R^{2''}$ denotes pyridinyl, thienyl, phenyl or substituted phenyl which is monosubstituted or disubstituted by halogen, alkyl, cycloalkyl, alkoxy, difluoromethoxy, difluoromethylthio, trifluoromethoxy, trifluoromethylthio, trifluoroethoxy, alkoxyalkoxy, cycloalkylalkoxy, alkoxyalkyl, alkylthioalkoxy, alkylsulphinylalkoxy, alkylsulphonylalkoxy, alkoxyalkylthio, alkoxyalkylsulphinyl, alkoxyalkylsulphonyl, alkylthioalkyl, alkylsulphinylalkyl, alkylsulphonylalkyl and dialkylaminoalkoxy, and
$R^3$ stands for $R^{3'}$ when Y denotes the group A and for $R^{3''}$ when R denotes the group B, where
$R^{3'}$ denotes hydrogen, difluoromethoxy, difluorometh- (Abstract continued on next page.)

ylthio, trifluoromethoxy, trifluoromethylthio, trifluoroethoxy, alkoxylalkoxy, alkoxyalkyl, alkylthioalkoxy, alkylsulphinylalkoxy, alkylsulphonylalkoxy, alkoxyalkylthio, alkoxyalkylsulphinyl, alkoxyalkylsulphonyl, alkylthioalkyl, alkylsulphinylalkyl, alkylsulphonylalkyl or dialkylaminoalkoxy, and $R^{3''}$ denotes hydrogen, alkoxy, halogen, difluoromethoxy, difluoromethylthio, trifluoromethoxy, trifluoromethylthio, trifluoroethoxy, alkoxyalkoxy, alkoxyalkyl, alkylthioalkoxy, alkylsulphinylalkoxy, alkylsulphonylalkoxy, alkoxyalkylthio, alkoxyalkylsulphinyl, alkoxyalkylsulphonyl, alkylthioalkyl, alkylsulphinylalkyl, alkylsulphonylalkyl or dialkylaminoalkoxy, or a physiologically tolerable hydrolysable derivative thereof, in which the hydroxyl group in the 2-position of the 3-aminopropoxy side chain is present in esterified form, and also their tautomeric forms and their salts and also acid addition salts, where in all cases previously mentioned alkyl of the alkyl groups or of alkyl moieties or alkylene moieties of groups in each case denotes straight-chain or branched alkyl or alkylene having 1 to 6 carbon atoms and cycloalkyl has 3 to 7 carbon atoms, with the proviso that if $R^{2'}$ denotes pyridinyl or thienyl, $R^{3'}$ does not denote hydrogen, but one of the other $R^3$ radicals mentioned show positive inotropic, vasodilatory and antiarrhythmic action and are suitable for the treatment of cardiac insufficiency, cardiac arrhythmias and hypertonia, coronary heart disease and peripheral and central arterial circulatory disturbances.

4 Claims, No Drawings

NEW INDOLYLPROPANOLS, PROCESSES FOR THEIR PREPARATION AND THEIR USE, AND PREPARATIONS CONTAINING THE COMPOUNDS

DESCRIPTION

The invention relates to new substituted indolylpropanols of the formula I

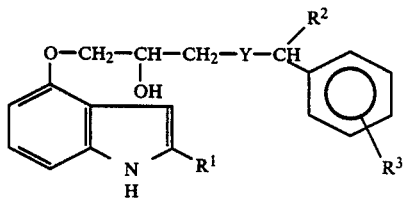

in which
$R^1$ denotes a cyano, carboxamido, alkoxycarbonyl, hydroxyl or acetyl group,
Y stands for the group A

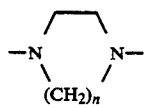

wherein n is the number 2 or 3, or the group B,

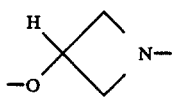

$R^2$ stands for $R^{2'}$ when Y denotes the group A and for $R^{2''}$ when Y denotes the group B, where
$R^{2'}$ denotes pyridinyl, thienyl or substituted phenyl which is monosubstituted or disubstituted by difluoromethoxy, difluoromethylthio, trifluoromethoxy, trifluoromethylthio, trifluoroethoxy, alkoxyalkoxy, cycloalkylalkoxy, alkoxyalkyl, alkylthioalkoxy, alkylsulphinylalkoxy, alkylsulphonylalkoxy, alkoxyalkylthio, alkoxyalkylsulphinyl, alkoxyalkylsulphonyl, alkylthioalkyl, alkylsulphinylalkyl, alkylsulphonylalkyl and dialkylaminoalkoxy, and
$R^{2''}$ denotes pyridinyl, thienyl, phenyl or substituted phenyl which is monosubstituted or disubstituted by halogen, alkyl, cycloalkyl, alkoxy, difluoromethoxy, difluoromethylthio, trifluoromethoxy, trifluoromethylthio, trifluoroethoxy, alkoxyalkoxy, cycloalkylalkoxy, alkoxyalkyl, alkylthioalkoxy, alkylsulphinylalkoxy, alkylsulphonylalkoxy, alkoxyalkylthio, alkoxyalkylsulphinyl, alkoxyalkylsulphonyl, alkylthioalkyl, alkylsulphinylalkyl, alkylsulphonylalkyl and dialkylaminoalkoxy, and
$R^3$ stands for $R^{3'}$ when Y denotes the group A and for $R^{3''}$ when Y denotes the group B, where
$R^{3'}$ denotes hydrogen, difluoromethoxy, difluoromethylthio, trifluoromethoxy, trifluoromethylthio, trifluoroethoxy, alkoxyalkoxy, alkoxyalkyl, alkylthioalkoxy, alkylsulphinylalkoxy, alkylsulphonylalkoxy, alkoxyalkylthio, alkoxyalkylsulphinyl, alkoxyalkylsulphonyl, alkylthioalkyl, alkylsulphinylalkyl, alkylsulphonylalkyl or dialkylaminoalkoxy, and $R^{3''}$ denotes hydrogen, alkoxy, halogen, difluoromethoxy, difluoromethylthio, trifluoromethoxy, trifluoromethylthio, trifluoroethoxy, alkoxyalkoxy, alkoxyalkyl, alkylthioalkoxy, alkylsulphinylalkoxy, alkylsulphonylalkoxy, alkoxyalkylthio, alkoxyalkylsulphinyl, alkoxyalkylsulphonyl, alkylthioalkyl, alkylsulphinylalkyl, alkylsulphonylalkyl or dialkylaminoalkoxy,
or a physiologically tolerable hydrolysable derivative thereof, in which the hydroxyl group in the 2-position of the 3-aminopropoxy side chain is present in esterified form, and also their tautomeric forms and their salts and also acid addition salts, where in all cases previously mentioned alkyl of the alkyl groups or of alkyl moieties or alkylene moieties of groups in each case denotes straight-chain or branched alkyl or alkylene having 1 to 6 carbons atoms and cycloalkyl has 3 to 7 carbon atoms, with the proviso that if $R^{2'}$ denotes pyridinyl or thienyl, $R^{3'}$ does not denote hydrogen, but one of the other $R^3$ radicals mentioned, and also processes for their preparation and their use and preparations which contain these compounds.

Physiologically hydrolysable derivatives are derivatives which are cleaved under physiological conditions to form the corresponding compounds which have a hydroxyl group in the 2-position of the propoxy side chain.

A group of such derivatives in esterified form of the compounds of the formula I consists e.g. of the compounds of the formula Ia

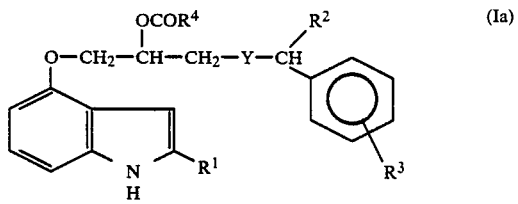

wherein
$R^1$, $R^2$, $R^3$ and Y have the abovementioned meaning, and
$R^4$ stands for alkyl having 1 to 12 carbon atoms, cycloalkyl having 3 to 7 carbon atoms, phenyl, phenylalkyl having 7 to 12 carbon atoms, phenyl or phenylalkyl having 7 to 12 carbon atoms which are monosubstituted in the phenyl ring by alkyl having 1 to 4 carbon atoms, phenyl or phenylalkyl having 7 to 12 carbon atoms which are monosubstituted or disubstituted in the phenyl ring by identical or different halogen having an atomic number from 9 to 35, or phenyl or phenylalkyl having 7 to 12 carbon atoms which are monosubstituted, disubstituted or trisubstituted in the phenyl ring by identical or different alkoxy having 1 to 4 carbon atoms.

The compounds of the formula I are preferred in which the hydroxyl group in the 2-position of the propoxy side chain is present in unesterified form.

If $R^{2'}$ represents pyridinyl or thienyl, Y stands for A and $R^1$ and also n have the meaning indicated, $R^{3'}$ does not denote hydrogen, but one of the other $R^3$ radicals mentioned. Compounds of the formula I in which Y denotes the group A and in which $R^3$ denotes hydrogen and $R^{2'}$ at the same time denotes pyridinyl or thienyl are thereby excluded.

Particularly preferred are the compounds of the formulae I or Ia, in which Y denotes the group B.

For the sake of simplicity, the compounds according to the invention are defined in only one tautomeric form represented by formula I. However, the invention applies to all tautomeric forms of the compounds. In particular, the oxindole form of the indole group substituted in the 2-position by hydroxyl is included.

Although pharmaceutically tolerable salts and acid addition salts of the new compounds of the formulae I and Ia and their tautomeric forms are preferred, all salts are within the range of the invention. All salts are valuable for the preparation of the compounds, even when the specific salt is only desired as an intermediate, such as, for example, when the salt is only formed for the purposes of purification or identification or when it is used as an intermediate in the preparation of a pharmaceutically tolerable salt, for example by ion exchange procedures.

The compounds of the general formula I and their salts contain asymmetrical carbon atoms. The invention therefore also relates to the various optical isomers and diastereomers as well as the salts and addition salts of these compounds with acids. The racemates can be separated into their optical antipodes by methods which are known per se.

Preferred compounds are those in which the asymmetrical carbon atom $C^{(1)*}$ possesses the S configuration in the propanolamine moiety of the formula I.

Compounds which are structurally related to the compounds of the present invention are described in European Patent Specification No. 25,111 and German Offenlegungsschrift 3,524,955. The compounds of the present invention are, however, neither specifically disclosed nor suggested by these disclosures.

Unless indicated otherwise, the alkyl groups and alkyl moieties or alkylene moieties of groups according to the invention can be straight-chain or branched and they each possess 1 to 6 carbon atoms, preferably 1 to 4 carbon atoms, in particular 1 to 2 carbon atoms. Examples of such one or more alkyl or alkylene-containing groups are alkoxy, alkoxyalkoxy, alkoxyalkyl, alkylthioalkoxy, alkoxyalkylthio or dialkylalkoxy. Preferred alkyl or alkene moieties are methyl, ethyl, n-propyl, isopropyl, butyl or correspondingly methylene, ethylene, n- or isopropylene and butylene.

Cycloalkylalkoxy groups according to the invention, e.g. $R^2$, $R^{2'}$ and $R^{2''}$, possess 4 to 13 carbon atoms, in particular 4 to 9 carbon atoms.

The alkoxy radicals of the cycloalkylalkoxy groups have 1 to 6 carbon atoms, methylene, ethylene and propylene being preferred as alkylene radicals of the alkoxy radicals.

Cycloalkyl groups according to the invention, e.g. $R^{2''}$, and cycloalkyl moieties such as cycloalkyl radicals of cyclo-alkylalkoxy groups possess 3 to 7 carbon atoms, in particular 3 to 6 carbon atoms. Cyclopropyl and cyclohexyl are particularly preferred.

Halogen radicals $R^{2''}$ and $R^{3''}$ are preferably F, Cl, Br, in particular F or Cl. Alkyl or alkyl moieties of the alkoxy group of the substituents $R^{2''}$ and $R^{3''}$ are $C_{1-6}$-alkyl, preferably methyl, ethyl, n- and isopropyl and butyl.

Preferred $R^{3''}$ radicals are hydrogen, alkoxy and halogen, in particular, however, hydrogen.

Preferred alkoxy groups of the alkoxycarbonyl group $R^1$ possess 1 to 6, preferably 1 to 4, carbon atoms. Particularly preferred are methoxy and ethoxy groups. Preferably $R^1$ is cyano.

Trifluoroethoxy radicals of $R^2$, $R^{2'}$ and $R^{2''}$ or $R^3$ are preferably $F_3CCH_2O-$ radicals.

Pyridinyl is preferably pyridin-4-yl and thienyl is preferably thien-3-yl.

Preferably, $R^2$ is phenyl or substituted phenyl, in particular, however, phenyl, when Y is the group B. The phenyl group can carry one or two of the substituents mentioned, which can be identical or different. If the phenyl groups are disubstituted, then the substituents are preferably identical.

Substituted phenyl groups $R^2$, $R^{2'}$ and $R^{2''}$ are preferably substituted in the 3- and/or 4-position with the indicated substituents, in particular monosubstituted in the 4-position. Similarly, the radical $R^3$ is preferably situated in the 3- or 4-position, in particular in the 4-position.

Preferably, $R^3$ is hydrogen. Particularly preferred compounds of the formula I or Ia are those in which Y denotes the group B and $R^3$ denotes hydrogen and the other radicals have the indicated meaning, in particular, however, $R^2$ and $R^{2''}$ are then phenyl.

Alkoxyalkoxy, alkoxyalkyl, alkylthioalkoxy, alkylsulphinylalkoxy, alkylsulphonylalkoxy, alkoxyalkylthio, alkoxyalkylsulphinyl, alkoxyalkylsulphonyl, alkylthioalkyl, alkylsulphinylalkyl, alkylsulphonylalkyl or dialkylaminoalkoxy substituents $R^3$ or those substituents of the phenyl group of the radical $R^2$ preferably possess 2–6, in particular 2–4 or 3–6 or 3–4 or also 2 carbon atoms. Preferred alkyl or alkylene moieties in these radicals are methyl, ethyl, n-propyl, isopropyl or correspondingly methylene, ethylene and propylene. They are preferably substituted terminally. Particularly preferred radicals of this type are alkoxyethoxy, alkoxymethyl, alkylthioethoxy, alkylsulphinylethoxy, alkylsulphonylethoxy, alkoxyethylthio, alkoxyethylsulphinyl, alkoxyethylsulphonyl, alkylthiomethyl, alkylsulphinylmethyl, alkylsulphonylmethyl and 2-dimethylaminoethoxy.

Particularly preferred $R^3$ radicals and substituents of the phenyl nucleus of $R^2$, $R^{2'}$ and $R^{2''}$ are difluoromethoxy and alkoxyalkyl, preferably alkoxyethoxy, in particular methoxyethoxy and alkoxyalkyl, preferably alkoxymethyl, in particular methoxymethyl. 2-Methoxyethoxy is particularly preferred.

The following compounds of the formula I, their salts and physiologically hydrolysable derivatives are preferred:

(a) 4-(3-((4-difluoromethoxyphenyl)phenylmethyl)piperazin-1-yl)-2-hydroxypropoxy)-1H-indole-2-carbonitrile (b) 4-(3-(4-(bis-4,4'-difluoromethoxy-diphenylmethyl)-piperazin-1-yl)-2-hydroxypropoxy)-1H-indole-2-carbonitrile (c) 4-(3-(4-((4-difluoromethoxyphenyl)(4-pyridinyl)methyl)piperazin-1-yl)-2-hydroxypropoxy)-1H-indole-2-carbonitrile (d) 4-(3-(4-((4-difluoromethoxyphenyl)(3-thienyl)methyl)piperazin-1-yl)-2-hydroxypropoxy)-1H-indole-2-carbonitrile (e) 4-(3-(4-((4-difluoromethoxyphenyl)phenylmethyl)-piperazin-1-yl)-2-hydroxypropoxy)-1H-indole-2(3H)-one (f) 4-(3-(4-((4-(2-methoxyethoxy)-phenyl)phenylmethyl)piperazin-1-yl)-2-hydroxypropoxy)-1H-indole-2-carbonitrile (g) 4-(3-(4-((4-methoxymethylphenyl)phenylmethyl)-piperazin-1-yl)-2-hydroxypropoxy)-1H-indole-2-carbonitrile (h) 4-(3-(1-diphenylmethyl-azetidin-3-oxy)-2-hydroxypropoxy)-1H-indole-2-carbonitrile The compounds (a), (f) and preferably (h) are particularly preferred, in particular with the S configuration n the $C^{(1)*}$ in the propanolamine moiety.

The compounds of the formula I according to the invention, their physiologically tolerable salts and acid addition salts and also their physiologically hydrolysable derivatives are therapeutic active compounds, possess a high pharmacological action and are valuable medicaments. In particular, they show positive inotropic, vasodilatory and antiarrhythmic action and are suitable for the treatment of cardiac insufficiency, cardiac arrhythmias and hypertonia, coronary heart diseases and peripheral and central arterial circulatory disturbance.

The compounds of the present invention can be used in humans orally or parenterally in a dosage of 1-800 mg, preferably 10-200 mg, particularly preferably 20-100 mg per day, in particular in subdivided doses, for example three times daily. These dosages are advantageous for the treatment of the previously mentioned diseases, in particular cardiac insufficiency and/or hypertonia and arrhythmias.

The positive inotropic action of the compounds according to the invention was determined on guinea-pig papillary muscle (Naunyn-Schmiedeberg's Arch. Pharmacol. 304, 37, 1978). The concentration of the substance in the organ bath was $10^{-4}$ mol/l in each case. The maximum percentage increase of the contraction amplitude was determined on three papillary muscles in each case and was at least 50%.

Accordingly to the invention, pharmaceutical compositions are provided which contain a compound of the formula I or the derivatives hydrolysable under physiological conditions to give the compounds according to the invention, such as e.g. esters or their pharmaceutically tolerable salts, together with a pharmaceutically tolerable diluent or excipient.

The compounds according to the invention can be mixed with the customary pharmaceutically tolerable diluents or excipients and if appropriate with other auxiliaries and, for example, can be administered orally or parenterally. They can be administered orally in the form of tablets, dragees, syrups, suspensions and liquids or parenterally in the form of solutions or suspensions. Preparations to be administered orally can contain one or more additives such as sweeteners, aromatizers, colorants and preservatives. Tablets may contain the active compound mixed with customary pharmaceutically tolerable auxiliaries, for example inert diluents such as calcium carbonate, sodium carbonate, lactose and talc, granulating agents and agents which promote the disintegration of the tablets on oral administration such as starch or alginic acid, binders such as starch or gelatin, lubricants such as magnesium stearate, stearic acid and talc.

Suitable excipients are, for example, lactose, gelatin, maize starch, stearic acid, ethanol, propylene glycol, ethers of tetrahydrofurfuryl alcohol and water.

The tablets may be coated by known procedures in order to delay disintegration and absorption in the gastrointestinal tract, by means of which the activity of the active compound can be extended over a longer time span. Likewise, in suspensions the active compound may be mixed with auxiliaries which are customary for the preparation of such compositions, for example suspending agents such as methylcellulose, tragacanth or sodium alginate, wetting agents such as lecithin, polyoxyethylene stearate and polyoxyethylene sorbitan monooleates and preservatives such as ethyl parahydroxybenzoate. Capsules may contain the active compound as the only component or mixed with a solid diluent such as calcium carbonate, calcium phosphate or kaolin. The injectable preparations are likewise formulated in a manner known per se. The pharmaceutical preparations may contain the active compound in an amount from 0.1 to 90%, in particular 1 to 90%, the residue being an excipient or additive. With respect to preparation and administration, solid preparations such as tablets and capsules are preferred. Preferably, the preparations contain the active compound in an amount from 5-50 mg.

The new compounds of the general formula I in which Y denotes the group A and $R^1$, $R^2$, $R^3$ and n have the meaning indicated can be prepared by reaction of the known compounds of the formula II

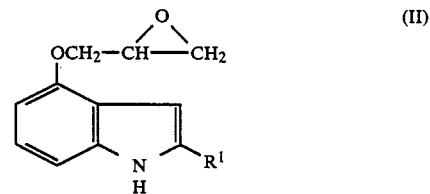

in which $R^1$ denotes a cyano, carboxamido, alkoxycarbonyl, hydroxyl or acetyl group, with piperazine derivatives of the formula III

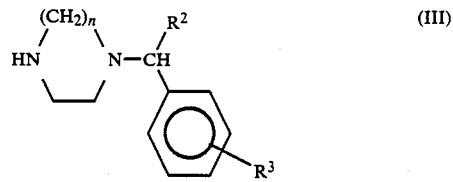

in which $R^2$, $R^3$ and n have the meaning indicated. The compounds of the formula III can be prepared by known processes or in analogy to known processes.

The reaction of the compounds of the formula II with the compounds of the formula III is preferably carried out in an alcohol such as ethanol or propanol or in a suitable ether such as dioxane or without solvent in the melt of the components. Suitable temperatures are between 20° C. to 200° C., the reaction being expediently carried out at the reflux temperature of the reaction mixture, if a solvent is present.

The compounds of the formula I, in which $R^1$ denotes a nitrile group and $R^2$, $R^3$ and Y have the abovementioned meaning, can be prepared by reaction of compounds of the formula I, in which $R^1$ denotes a carboxamido group. For these reactions, suitable dehydrating reagents, such as e.g. trifluoroacetic anhydride in suitable inert solvents such as, e.g. dioxane are used, in the presence of a weak base such as pyridine or triethylamine at temperatures between 0° C. and room temperature, preferably at room temperature.

The compounds of the formula III can be prepared by known processes by reaction of compounds of the formula IV

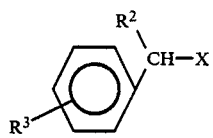

in which $R^2$ and $R^3$ have the abovementioned meaning and X denotes a leaving group such as e.g. bromine, chlorine or a tosylate or mesylate group, with piperazine in the case where n denotes 2 or homopiperazine in the case where n denotes 3, in a suitable solvent such as e.g. dimethylformamide at temperatures between 0° C. and the boiling temperature of the reaction mixture.

The compounds of the formula IV are obtained in analogy to known processes from the corresponding alcohols of the formula V

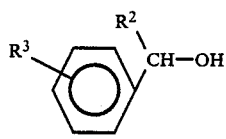

in which $R^1$ and $R^2$ have the abovementioned meaning.

In the case where X denotes a halogen atom, for example chlorine, the alcohols of the formula V are reacted with a chlorinating agent such as e.g. thionyl chloride without solvent or in an inert solvent such as e.g. toluene, at temperatures between room temperature and the boiling temperature of the solvent. The bromine derivatives of the formula IV can be obtained by reaction with phosphorus tribromide.

The alcohols of the formula V can be prepared by reaction of Grignard compounds of the formula VI or VIa, in which X' denotes a chlorine or bromine atom, with aldehydes of the formula VII or VIIa

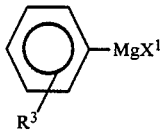

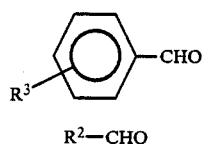

in analogy to known processes (Houben Weyl XIII/2a, 289, 302) or carried out by reduction of ketones of the formula VIII

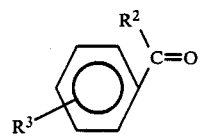

in which $R^2$ and $R^3$ have the abovementioned meaning, with reductants such as zinc or sodium borohydride in suitable solvents such as e.g. methanol or ethanol at room temperature or the boiling temperature of the solvent, preferably at room temperature.

The compounds of the formula VIII, in which $R^2$ denotes a phenyl nucleus which is unsubstituted or substituted by a difluoromethoxy group, and $R^3$ denotes a difluoromethoxy group, can be prepared from corresponding monohydroxy- or dihydroxybenzophenones by reaction with difluorochloromethane in a mixture of dioxane and sodium hydroxide solution at temperatures between room temperature and the boiling temperature of the mixture, preferably at 50°–70° C. (Lit.: DE 3,017,339). The difluoromethylthio derivatives of the formula VIII can be obtained analogously.

The compounds of the formula I in which Y denotes the group B can be prepared by reaction of the known indole derivatives of the formula IX

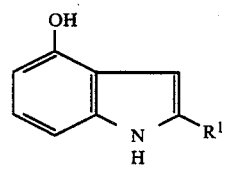

with compounds of the formula X

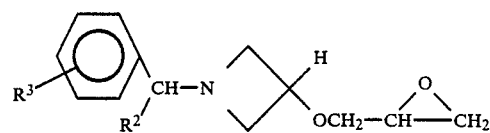

where $R^1$, $R^2$ and $R^3$ have the abovementioned meaning. The reactions can be carried out in aqueous dioxane or in other suitable solvents in the presence of alkali, preferably sodium hydroxide solution. The reaction temperature can be between room temperature and the boiling temperature of the mixture. It is preferably between 50° and 70° C.

The compounds of the formula X, in which $R^2$ and $R^3$ have the abovementioned meaning, can be prepared by reaction of compounds of the formula XI

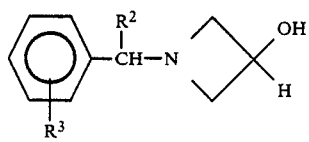

which are known or which can be prepared by known processes in which $R^2$ and $R^3$ have the abovementioned meaning, with epichlorohydrin in a suitable solvent, such as e.g. dimethyl sulphoxide in the presence of alkali, preferably sodium hydroxide solution, at temperatures between 0° C. to 50° C., preferably room temperature.

The compounds of the general formula XI can be prepared by reaction of benzhydrylamines of the general formula XII

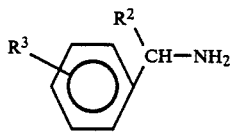

in which $R^2$ and $R^3$ have the meaning indicated, with epichlorohydrin in a suitable solvent such as methanol, preferably at room temperature to the boiling temperature of the mixture, in particular at 70° C.

The compounds of the formula XII can be prepared by processes which are known per se or analogously to the processes described here or analogously to processes which are known per se (literature: Beilstein, Fourth Supplement, 12, System Number 1734 and Najer et al., Bl. 1959, 352–355).

Necessary esterification, if appropriate, of the hydroxyl group in the 3-aminopropoxy side chain can be carried out analogously to methods known for the preparation of analogous esters of 3-amino-2-hydroxypropoxyaryl compounds, if necessary using selective conditions if other reactive groups are present.

The starting materials used are known or can be prepared by processes which are known per se or analogously to the processes described here or analogously to processes which are known per se.

The compounds of the general formula I can be both bases and acids or amphoteric and can therefore be isolated from the reaction mixtures in the form of their salts or acid addition salts. As bases, they can be converted into salts by known processes using suitable inorganic or organic acids or as acids with bases, can form, salts.

Physiologically tolerable salts or acid addition salts are preferred. For this purpose, for example, sulphuric acid or hydrohalic acids, for example hydrochloric acid, are suitable as inorganic acids, and, for example, fumaric acid, maleic acid, citric acid and tartaric acid are suitable as organic acids. For preparation, the alcoholic solution of a suitable acid is added to the hot alcoholic solution of the base and the salt is obtained after addition of ether. Preferred salts are the alkali metal, alkaline earth metal and ammonium salts of the compounds of the formula I which are obtained with the corresponding bases, in particular sodium hydroxide or potassium hydroxide.

The compounds of the formula I according to the invention exhibit a centre of chirality on carbon atom 2 of the propoxy side chain and can, depending on the substituents, possess further asymmetric carbon atoms and therefore exist as racemates and diastereomers. Diastereomers can be resolved into their racemic modifications in a known manner based on the physicochemical differences of their components. Racemates can be resolved by known methods, for example by recrystallizing in optically active solvents, by microorganisms or reaction with an optically active acid or base which forms a salt with the racemic compound, resolution of the diastereomers by fractional crystallization and releasing the enantiomers by suitable agents. Particularly suitable optically active acids are, for example, the d and l forms of tartaric acid, ditoluyltartaric acid, malic acid, mandelic acid, camphorsulfonic acid or pyrrolidonecarboxylic acid. Suitable optically active bases are alpha-phenylethylamine, methylamine, ephedrine, brucine and quinine. Advantageously, the more active of the antipodes is isolated. According to the invention, however, it is also possible to obtain the pure enantiomers by asymmetric synthesis.

The following examples serve to illustrate the invention.

EXAMPLE 1

4-(3-(4-((4-Difluoromethoxyphenyl)phenylmethyl)piperazin-1-yl)-2-hydroxypropoxy)-1H-indole-2-carbonitrile 4.0 g of 4-(3-(4-((4-difluoromethoxyphenyl)phenylmethyl)piperazin-1-yl)-2-hydroxypropoxy)-1H-indole-2-carboxamide are dissolved in a mixture of 36 ml of dioxane and 1.7 g of pyridine and 1.6 ml of trifluoroacetic anhydride in 10.5 ml of dioxane are added at 10° C. After standing for two hours at room temperature, the mixture is stirred into ice water. It is then extracted with methylene chloride, washed with water, and the organic phase is dried over sodium sulphate and concentrated. The residue is purified by column chromatography on silica gel (eluent, chloroform/methanol 40:2).
Yield 1.1 g (30%).
M.p.: 99°–103° C. (Z) as the trifluoroacetate.

EXAMPLE 1a 4-(3-(4-((4-Difluoromethoxyphenyl)phenylmethyl)piperazin-1-yl)-2-hydroxypropoxy)-1H-indole-2-carbonitrile 2.5 g of 4-(2,3-epoxypropoxy)-1H-indole-2-carbonitrile and 3.7 g of 1-((4-difluoromethoxyphenyl)phenylmethyl)piperazine are dissolved in 50 ml of methanol and heated for 3 hours under reflux. The mixture is then concentrated to dryness in vacuo and the residue is triturated with hexane, filtered off with suction and purified by column chromatography on silica gel (eluent: chloroform/methanol 40:2).
Yield: 1.2 g.
M.p.: 93°–95° C.

EXAMPLE 2

4-(3-(4-((4-Difluoromethoxyphenyl)phenylmethyl)piperazin-1-yl)-2-hydroxypropoxy)-1H-indole-2-carboxamide 3.45 g of 4-(2,3-epoxypropoxy)-1H-indole-2-carboxamide and 4.70 g of 1-((4-difluoromethoxyphenyl)phenylmethyl)piperazine are dissolved at 40° C. in 75 ml of methanol. The mixture is then concentrated to dryness in vacuo, the syrupy residue is heated at 80° C. for 15 minutes and, after cooling, the solidified product is triturated with hexane and filtered off with suction.
Crude yield: 6.7 g (81%);
After column chromatographic purification.
Yield: 2.68 g (32.5%).
M.p.: 102°–106° C. (Z).

EXAMPLE 3

1-((Difluoromethoxyphenyl)phenylmethyl)piperazine 4.9 g of potassium carbonate and 17.5 g of anhydrous piperazine are added to 18.3 g of 4-difluoromethoxybenzhydryl chloride in 50 ml of dimethylformamide and the mixture is stirred at room temperature for 12 hours. 0.5 l of water is then added to the reaction mixture, the latter is extracted with chloroform and the chloroform phase is washed with 1N hydrochloric acid. The aqueous phase is rendered alkaline and extracted using chloroform. The organic phase is dried and evaporated. 19.5 g of 1-((difluoromethoxyphenyl)phenylmethyl)piperazine are obtained as a pale yellow oil.

EXAMPLE 4

4-Difluoromethoxybenzhydryl chloride 55 g of 4-difluoromethoxybenzhydrol are dissolved in 440 ml of chloroform, the mixture is cooled to 0° C. and 17.5 ml of thionyl chloride in 220 ml of chloroform are added. The mixture is allowed to stand for 24 hours at room temperature and excess thionyl chloride and chloroform are removed by distillation. 47 g (80%) of 4-difluoromethoxybenzhydryl chloride are obtained as a yellow oil.

EXAMPLE 5

4-Difluoromethoxybenzhydrol 60 g of 4-difluoromethoxybenzophenone are reduced using sodium borohydride in 400 ml of methanol at 40° C. After an hour, the mixture is concentrated to dryness, 1.2 l of water is added to the contents of the flask and the mixture is extracted with chloroform. The organic phase is then dried and concentrated.

Yield: 55 g (91%) of 4-difluoromethoxybenzhydrol as a pale brown oil.

EXAMPLE 6

4-Difluoromethoxybenzophenone 100 g of 4-hydroxybenzophenone and 200 g of sodium hydroxide are dissolved in a mixture of 1 l of water and 500 ml of dioxane. The mixture is heated to 70° C. and a vigorous stream of difluorochloromethane (Frigen 22) is introduced. After 2 hours, the mixture is cooled to room temperature and 1 l of water is added to the contents of the flask. The mixture is extracted three times using 1.2 l of chloroform each time, the chloroform phase is extracted by shaking with 1N sodium hydroxide solution, washed with water and the organic phase is dried using potassium carbonate. After stripping off the solvent and subsequent distillation under vacuum, 60 g (48%) of 4-difluoromethoxybenzophenone are obtained as a pale yellow oil.

B.p. 131°–135°, 0.7–1.0 mbar.

EXAMPLE 7

1-(Diphenylmethyl)-3-(2,3-epoxypropoxy)azetidine 37.5 g of diphenylmethylazetidin-3-ol are dissolved at room temperature in a mixture of 250 ml of dimethyl sulphoxide and 150 ml of 5% strength sodium hydroxide solution, 65 ml of epichlorohydrin are added and the mixture is allowed to stand for 3 days at room temperature. The reaction mixture is extracted using 300 ml of methylene chloride, and the organic phase is dried over sodium sulphate and evaporated. The crude product is distilled in vacuo.

Yield: 29.0 g of 1-(Diphenylmethyl)-3-(2,3-epoxypropoxy)azetidine.

B.p. 174°–176° C. 0.2 mbar.

EXAMPLE 8

4-(3-(1-Diphenylmethylazetidin-3-oxy)-2-hydroxypropoxy)-1H-indole-2-carboxamide 8.8 g of 4-hydroxy-1H-indole-2-carboxamide are dissolved in 250 ml of 0.8 percent strength sodium hydroxide solution and a solution of 16.3 g of 1-(diphenylmethyl)-3-(2,3-epoxypropoxy)azetidine in 250 ml of dioxane is added. The mixture is allowed to stand for 4 hours at room temperature and then warmed to 60° C. for a further 20 hours. The reaction mixture is then stirred into 1 l of ice water and extracted twice with 500 ml of methylene chloride each time. The organic phase is dried using potassium carbonate and the solvent is removed by distillation in vacuo. The residue is triturated twice with 100 ml of diisopropyl ether each time and filtered off with suction.

Yield: 7.1 g of 4-(3-(1-Diphenylmethylazetidin-3-oxy)-2-hydroxypropoxy)1H-indole-2-carboxamide.

M.p. 186° C.

EXAMPLE 9

4-(3-(1-Diphenylmethylazetidin-3-oxy)-2-hydroxypropoxy)1H-indole-2-carbonitrile 10.0 g of 4-(3-(1-diphenylmethylazetidin-3-oxy)-2-hydroxypropoxy)-1H-indole-2-carboxamide are dissolved in a mixture of 112 ml of dioxane and 10 g of pyridine and 10 ml of trifluoroacetic anhydride in 10 ml of dioxane are added at 10° C. After standing for two hours at room temperature, the mixture is stirred into ice water. The mixture is extracted using methylene chloride, washed first with dilute NaOH, then with water, and the organic phase is dried over sodium sulphate and concentrated. The residue is purified by column chromatography on silica gel (eluent: chloroform).

Yield: 9.3 g (41%) of 4-(3-(1-diphenylmethylazetidin-3-oxy)-2-hydroxypropoxy)-1H-indole-2-carbonitrile.

M.p.: 83°–85° C.

EXAMPLE 10

Preparation of ampoules

Ampoules which contain the constituents mentioned in the following can be prepared in a known manner. The active compound is dissolved in water and 1,2-propanediol and filled into glass ampoules under nitrogen.

4-(3-(4-((4-(2-methoxyethoxy)-phenyl)-phenylmethyl)-piperazin-1-yl)-2-hydroxypropoxy)-1H-indole-2-carbonitrile: 2 mg.

1,2-propanediol: 0.8 ml.

distilled water to make up to: 2.0 ml.

EXAMPLE 11

Preparation of tablets and capsules

Tablets and capsules which contain the constituents indicated below are prepared by known procedures. These are suitable in dosage amounts of one tablet or capsule in each case three times daily for the treatment of the previously mentioned diseases, in particular cardiac insufficiency.

| Constituents | Weight (mg) | |
|---|---|---|
| | Tablet | Capsule |
| 4-(3-(4-((4-(2-methoxyethoxy)-phenyl)phenylmethyl)piperazin-1-yl)hydroxypropoxy)-1H-indole-2-carbonitrile | 30 | 10 |
| tragacanth | 10 | |
| lactose | 247.5 | 300 |
| maize starch | 25 | |
| talc | 15 | |
| magnesium stearate | 2.5 | |

EXAMPLE 12

Preparation of ampoules

Ampoules which contain the constituents mentioned in the following can be prepared in a known manner. The active compound is dissolved in water and 1,2-propanediol and filled into glass ampoules under nitrogen.

4-(3-(1-diphenylmethylazetidin-3-oxy)-2-hydroxypropoxy)-1H-indole-2-carbonitrile: 2 mg.
1,2-propanediol: 0.8 ml.
distilled water to make up to: 2.0 ml.

EXAMPLE 13

Preparation of tablets and capsules

Tablets and capsules which contain the constituents indicated below are prepared by known procedures. These are suitable in dosage amounts of one tablet or capsule in each case three times daily for the treatment of the previously mentioned diseases, in particular cardiac insufficiency.

| Constituents | Weight (mg) Tablet | Capsule |
|---|---|---|
| 4-(3-(1-diphenylmethylazetidin-3-oxy)-2-hydroxypropoxy)-1H-indole-2-carbonitrile | 30 | 10 |
| tragacanth | 10 | |
| lactose | 247.5 | 300 |
| maize starch | 25 | |
| talc | 15 | |
| magnesium stearate | 2.5. | |

The compounds of the formula I according to the invention indicated in the following table, in which Y denotes the group A (Examples 14–75) can be obtained analogously to the previous examples:

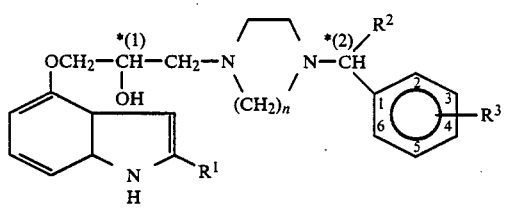

"rac" denotes racemic. Unless indicated otherwise by $R^4$, the 2-hydroxyl group of the propoxyamino side chain is present in unesterified form.

"- - -" denotes that no asymmetric carbon atom is present.

| Example | $R^1$ | $R^2$ | $R^3$ | n | Config. $C^{*(1)}$ | Config. $C^{*(2)}$ | m.p. °C. |
|---|---|---|---|---|---|---|---|
| 14 | CN | –C₆H₄–OCHF₂ | 4-OCHF₂ | 2 | rac | — | 80 |
| 15 | CN | –C₆H₄–OCHF₂ | H | 2 | S | S | |
| 16 | CN | –C₆H₄–OCHF₂ | H | 2 | S | R | |
| 17 | OH | –C₆H₄–OCHF₂ | H | 2 | rac | rac | |
| 18 | C(=O)–CH₃ | –C₆H₄–OCHF₂ | H | 2 | rac | rac | |
| 19 | CN | –C₆H₄–OCHF₂ | H | 3 | rac | rac | 75 |
| 20 | CN | –C₆H₄–OCHF₂ | 4-OCHF₂ | 3 | rac | — | |
| 21 | CN | 3-Pyridinyl | 4-OCHF₂ | 2 | rac | rac | |
| 22 | CN | 4-Pyridinyl | 4-OCHF₂ | 2 | rac | rac | |

-continued
| Example | R¹ | R² | R³ | n | Config. C*(1) | Config. C*(2) | m.p. °C. |
|---|---|---|---|---|---|---|---|
| 23 | CN | 2-Thienyl | 4-OCHF₂ | 2 | rac | rac | |
| 24 | CN | 3-Thienyl | 4-OCHF₂ | 2 | rac | rac | |
| 25 | CN | 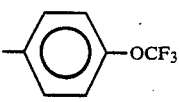 | H | 2 | rac | rac | |
| 26 | CN | 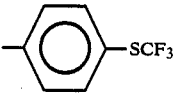 | H | 2 | rac | rac | |
| 27 | CN | 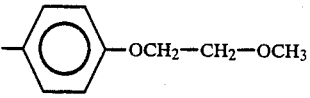 | H | 2 | rac | rac | 93–95 (Z) |
| 28 | CN | 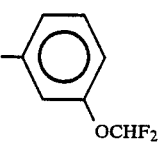 | 3-OCHF₂ | 2 | rac | — | |
| 29 | CN | 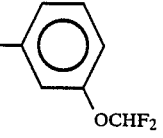 | H | 2 | rac | rac | |
| 30 | CN | 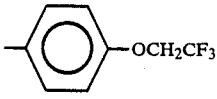 | H | 2 | rac | rac | |
| 31 | CN | 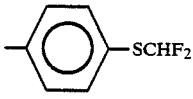 | H | 2 | rac | rac | |
| 32 | OH | 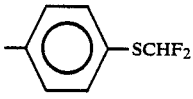 | H | 2 | rac | rac | |
| 33 | CN | 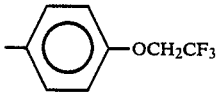 | H | 2 | rac | rac | 91–93 |
| 34 | CO₂Et | 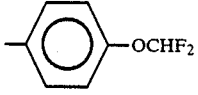 | H | 3 | rac | rac | |
| 35 | CONH₂ | 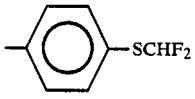 | 4-SCHF₂ | 2 | rac | — | |
| 36 | CN | 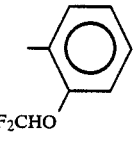 | 2-OCHF₂ | 2 | rac | — | 108–110 |

| Example | R¹ | R² | R³ | n | Config. C*(1) | Config. C*(2) | m.p. °C. |
|---|---|---|---|---|---|---|---|
| 37 | CN | phenyl-OCH₂—CH₂—OCH₃ (ortho) | H | 2 | rac | rac | 102–104 |
| 38 | CN | phenyl-OCH₂—CH₂—OC₂H₅ (para) | H | 2 | rac | rac | 89–91 |
| 39 | CN | phenyl-OCH₂—CH₂—O—CH(CH₃)₂ (para) | H | 2 | rac | rac | |
| 40 | CN | phenyl-OCH₂—CH₂—S—CH₃ (para) | H | 2 | rac | rac | 204–207 |
| 41 | CN | phenyl-OCH₂—CH₂—S(O)—CH₃ (para) | H | 2 | rac | rac | |
| 42 | CN | phenyl-OCH₂—CH₂—S(O)₂—CH₃ (para) | H | 2 | rac | rac | |
| 43 | CN | phenyl-OCH₂—CH₂—N(CH₃)₂ (para) | H | 2 | rac | rac | |
| 44 | CN | phenyl-CH₂—O—CH₃ (para) | H | 2 | rac | rac | |
| 45 | CN | phenyl-CH₂—O—C₂H₅ (para) | H | 2 | rac | rac | |
| 46 | CN | phenyl-CH₂—O—C₃H₇ (para) | H | 2 | rac | rac | |
| 47 | CN | phenyl-CH₂—CH₂—OCH₃ (para) | H | 2 | rac | rac | |
| 48 | CN | phenyl-S—CH₂—CH₂—OCH₃ (para) | H | 2 | rac | rac | |
| 49 | CN | phenyl-S(O)—CH₂—CH₂—OCH₃ (para) | H | 2 | rac | rac | |

| Example | R¹ | R² | R³ | n | Config. C*(1) | Config. C*(2) | m.p. °C. |
|---|---|---|---|---|---|---|---|
| 50 | CN | 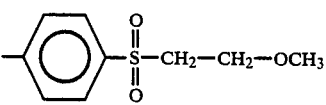 | H | 2 | rac | rac | |
| 51 | CN | 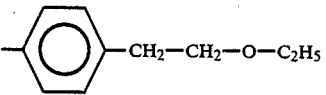 | H | 2 | rac | rac | |
| 52 | CN | 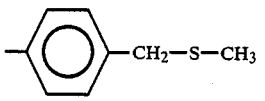 | H | 2 | rac | rac | |
| 53 | CN | 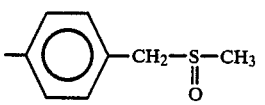 | H | 2 | rac | rac | |
| 54 | CN | 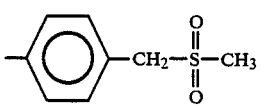 | H | 2 | rac | rac | |
| 55 | CN | 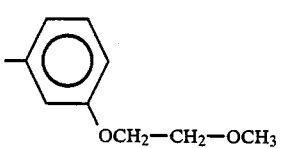 | H | 2 | rac | rac | 86–87 |
| 56 | CN | 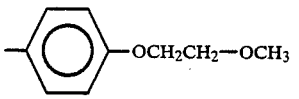 | H | 2 | S | S | |
| 57 | CN | 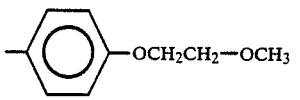 | H | 2 | S | R | |
| 58 | CN | 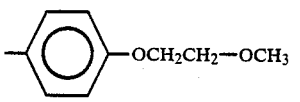 | H | 2 | S | rac | |
| 59 | CN | 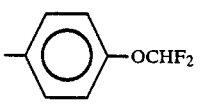 | H | 2 | S | rac | |
| 60 | CN | 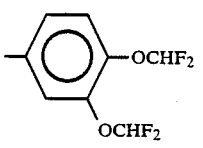 | H | 2 | rac | rac | |
| 61 | CN | 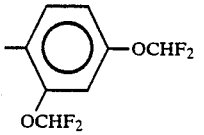 | H | 2 | rac | rac | |

-continued

| Example | R¹ | R² | R³ | n | Config. C*(1) | Config. C*(2) | m.p. °C |
|---|---|---|---|---|---|---|---|
| 62 | CN | phenyl with -OCH₂-CH₂-OCH₃ and OCH₂-CH₂-OCH₃ | H | 2 | rac | rac | |
| 63 | CN | phenyl with -OCH₂-CH₂-OCH₃ | 4-OCH₂-CH₂-OCH₃ | 2 | rac | — | 77-78 |
| 64 | CN | phenyl with -CH₂-OCH₃ | 4-CH₂-OCH₃ | 2 | rac | — | |
| 65 | C(=O)NH₂ | phenyl with -OCHF₂ | 4-OCHF₂ | 2 | rac | — | 93 |
| 66 | CN | phenyl with -OCHF₂ | H | 2 | S | rac | 86-93 |
| 67 | CN | phenyl with -OCH₂-cyclopropyl | H | 2 | rac | rac | 146-147 |
| 68 | CN | phenyl with -OCH₂-cyclohexyl | H | 2 | rac | rac | |
| 69 | C(=O)NH₂ | phenyl with -OCH₂-CH₂-OCH₃ | H | 2 | rac | rac | 95-96 |
| 70 | CN | phenyl with -OCH₂-CH₂-OCH₃ | H | 2 | R | rac | 113-123 |

For the preparation of the compound of Example 27, 4-(2-methoxyethoxy)benzophenone is obtained by reaction of 4-hydroxybenzophenone with 2-methoxyethyl chloride at 100° C. in the presence of sodium hydride in dimethylformamide. Further reaction takes place in accordance with Example 1-5. 4-(2-Methoxyethoxy)benzophenone is reduced to 4-(2-methoxyethoxy)benzhydrol using sodium borohydride. 4-(2-Methoxyethoxy)benzhydrol is reacted with thionyl chloride in chloroform to give 4-(2-methoxyethoxy)benzhydryl chloride. 4-(2-methoxyethoxy)benzhydryl chloride is reacted with piperazine in dimethylformamide in the presence of potassium carbonate to give 1-((4-(2-methoxyethoxy)phenyl)phenylmethyl)piperazine.

4-(2,3-Epoxypropoxy)-1H-indole-2-carboxamide is reacted with 1-((4-(2-methoxyethoxy)phenyl)phenylmethyl)piperazine to give 4-(3-(4-((4-(2-methoxyethoxy)phenyl)phenylmethyl)piperazin-1-yl)-2-hydroxypropoxy)-1H-indole-2-carboxamide. The compound obtained is reacted with trifluoroacetic anhydride in a mixture of dioxane and pyridine to give 4-(3-(4-((4-(2-methoxyethoxy)phenyl)phenylmethyl)piperazin-1-yl)-2-hydroxypropoxy)-1H-indole-2-carbonitrile.

The esterified compounds of the formula Ia can be obtained by reaction of corresponding compounds of the formula I with anhydrides of the formula R⁴COO-COR⁴ or acid halides of the formula R⁴COHal, in particular R⁴COCl, if appropriate in a solvent such as pyridine. The compound of Example 71 can be prepared by reaction of the compound of Example 27 with acetic anhydride at room temperature.

The following compounds of the formula Ia, in which Y denotes the group A, can be obtained by esterification of compounds of the formula I:

| Example | R¹ | R² | R³ | R⁴ | n | Config. C*(1) | Config. C*(2) | m.p.°C. |
|---|---|---|---|---|---|---|---|---|
| 71 | CN | —C₆H₄—OCH₂—CH₂—OCH₃ | H | CH₃ | 2 | rac | rac | |
| 72 | CN | —C₆H₄—OCH₂—CH₂—OCH₃ | H | cyclohexyl | 2 | rac | rac | |
| 73 | CN | —C₆H₄—OCHF₂ | H | phenyl | 2 | rac | rac | |
| 74 | CN | —C₆H₄—OCH₂CH₂OCH₃ | H | 4-CH₃-phenyl | 2 | rac | rac | |
| 75 | CN | —C₆H₄—OCHF₂ | H | CH₃ | 2 | rac | rac | 166–168 |

The compounds of the formula I according to the invention, in which Y denotes the group B indicated in the following table, (Examples 76–85) can be obtained analogously to the previous Examples (7–9):

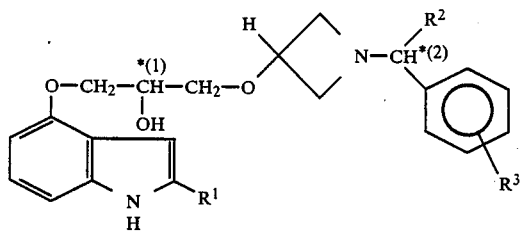

"rac" denotes racemic. Unless indicated otherwise by R⁴, the 2-hydroxyl group of the propoxyamino side chain is present in unesterified form.

"- - -" denotes that no asymmetrical carbon atom is present.

| Example | R¹ | R² | R³ | Config. C*(1) | Config. C*(2) | m.p. °C. |
|---|---|---|---|---|---|---|
| 76 | CN | Phenyl | 3-OCH₃ | rac | rac | |
| 77 | CN | Phenyl | 2-Cl | rac | rac | |
| 78 | CN | 4-Cl-Phenyl | 4-Cl | rac | — | |
| 79 | CN | Phenyl | 4-Cl | rac | rac | |
| 80 | CN | Phenyl | 4-OCH₃ | rac | rac | |
| 81 | CONH₂ | Phenyl | H | rac | — | 186 |
| 82 | CN | 4-P-Phenyl | 4-F | rac | — | 78–80 |
| 83 | CN | Phenyl | H | S | — | 79 |
| 84 | CN | Phenyl | O—(CH₂)₂OCH₃ | rac | rac | |

The following compound of the formula Ia, in which Y denotes the group B, can be obtained by esterification of compounds of the formula I:

| Example | R¹ | R² | R³ | R⁴ | Config. C*(1) | Config. C*(2) | m.p. °C. |
|---|---|---|---|---|---|---|---|
| 85 | CN | H | H | CH₃ | rac | | 61–63 |

We claim:

1. Substituted indolylpropanols of the formula I

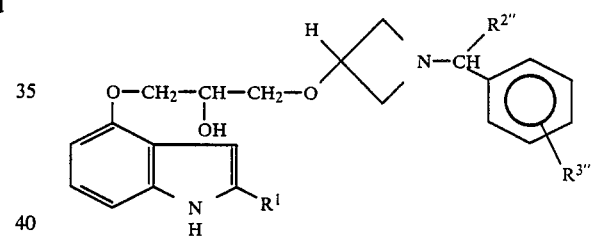

in which,
R¹ denotes a cyano, carboxamido, alkoxycarbonyl, hydroxyl or acetyl group,
R²″ denotes pyridinyl, thienyl, phenyl or substituted phenyl which is monosubstituted or disubstituted by halogen, alkyl, cycloalkyl, alkoxy, difluoromethoxy, difluoromethylthio, trifluoromethoxy, trifluoromethylthio, trifluoroethoxy, alkoxyalkoxy, cycloalkylalkoxy, alkoxyalkyl, alkylthioalkoxy, alkylsulphinylalkoxy, alkylsulphonylalkoxy, alkoxyalkylthio, alkoxyalkylsulphinyl, alkoxyalkylsulphonyl, alkylthioalkyl, alkylsulphinylalkyl, alkylsulphonylalkyl and dialkylaminoalkoxy, and $R^{3''}$ denotes hydrogen, alkoxy, halogen, difluoromethoxy, difluoromethylthio, trifluoromethoxy, trifluoromethylthio, trifluoroethoxy, alkoxyalkoxy, alkoxyalkyl, alkylthioalkoxy, alkylsulphinylalkoxy, alkylsulphonylalkoxy, alkoxyalkylthio, alkoxyalkylsulphinyl, alkoxyalkylsulphonyl, alkylthioalkyl, alkylsulphinylalkyl, alkylsulphonylalkyl or dialkylaminoalkoxy, or a physiologically tolerable hydrolysable derivative thereof in which the hydroxyl group in the 2-position of the 3-aminopropoxy side chain is present in esterified form, and also their tautomeric forms and their physiologically tolerable salts, where in all cases previously mentioned alkyl of the alkyl groups or of alkyl moieties or alkylene moieties of groups in each case denotes straight-chain or branched alkyl or alkylene having 1 to 6 carbon atoms and cycloalkyl has 3 to 7 carbon atoms.

2. The compound according to claim 1 which is 4-(3-(1-Diphenylmethylazetidin-3-oxy)-2-hydroxypropoxy)-1H-indole-2-carbonitrile.

3. A composition suitable for the treatment of cardiac insufficiency, cardiac arrhythmias, hypertonia, coronary heart diseases or peripheral or central arterial circulatory disturbances comprising an amount effective therefor of a compound or salt according to claim 1 and a pharmaceutically acceptable diluent.

4. A method of treating a ptient afflicted with cardiac insufficiency, cardiac arrhythmia, hypertonia, coronary heart disease or peripheral or central arterial circulatory disturbance comprising administering to such patient an amount effective therefor of a compound or salt according to claim 1.

* * * * *

UNITED STATES PATENT AND TRADEMARK OFFICE
CERTIFICATE OF CORRECTION

PATENT NO. : 4,935,414

DATED : June 19, 1990

INVENTOR(S) : Wolfgang Stenzel, et al

It is certified that error appears in the above-identified patent and that said Letters Patent is hereby corrected as shown below:

| | |
|---|---|
| Title Page, under "Other Publications", line 21 | Delete "1987" and substitute --1978-- |
| Title Page, "Abstract", line 2 from bottom of Title Page | Delete "R" and substitute --Y-- |
| Col. 24, line 44 | After "group," insert --Y stands for the group A |

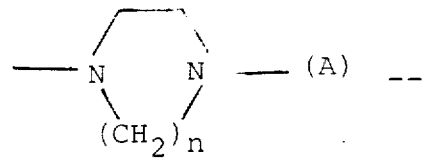

Signed and Sealed this

Twenty-first Day of July, 1992

Attest:

DOUGLAS B. COMER

Attesting Officer

Acting Commissioner of Patents and Trademarks